(12) United States Patent
Rehahn et al.

(10) Patent No.: US 8,293,957 B2
(45) Date of Patent: Oct. 23, 2012

(54) OLIGO-TETRACENES, PRODUCTION AND USE THEREOF

(75) Inventors: Matthias Rehahn, Fürth (DE); Michael Roth, Mainz (DE); Heinz Von Seggern, Bensheim (DE); Roland Schmechel, Darmstadt (DE); Marcus Ahles, Pfullingen (DE)

(73) Assignee: Dritte Patentportfolio Beteiligungsgesellschaft mbH & Co. KG, Schoenefeld/Waltersdorf (DE)

( * ) Notice: Subject to any disclaimer, the term of this patent is extended or adjusted under 35 U.S.C. 154(b) by 684 days.

(21) Appl. No.: 11/922,963

(22) PCT Filed: Jun. 21, 2006

(86) PCT No.: PCT/EP2006/005926
§ 371 (c)(1),
(2), (4) Date: Dec. 20, 2007

(87) PCT Pub. No.: WO2007/000268
PCT Pub. Date: Jan. 4, 2007

(65) Prior Publication Data
US 2008/0214838 A1 Sep. 4, 2008

(30) Foreign Application Priority Data
Jun. 25, 2005 (DE) .......................... 10 2005 029 574

(51) Int. Cl.
*C07D 409/04* (2006.01)
*C07D 407/04* (2006.01)
*C07D 403/04* (2006.01)
*C07C 15/38* (2006.01)

(52) U.S. Cl. ............. 585/26; 548/518; 549/42; 549/457

(58) Field of Classification Search ................... 257/40; 548/426; 549/42, 457
See application file for complete search history.

(56) References Cited

U.S. PATENT DOCUMENTS

| | | | |
|---|---|---|---|
| 2002/0177009 A1 | 11/2002 | Suzuki | 428/690 |
| 2003/0100779 A1 | 5/2003 | Vogel | 552/208 |
| 2004/0100188 A1 | 5/2004 | Hosokawa | 313/504 |
| 2004/0253389 A1 | 12/2004 | Suzuki | 428/1.1 |
| 2005/0012090 A1 | 1/2005 | Gerlach | 257/40 |
| 2005/0035333 A1 | 2/2005 | Gerlach | 252/500 |
| 2006/0105199 A1 | 5/2006 | Gerlach | 428/690 |

FOREIGN PATENT DOCUMENTS

| | | |
|---|---|---|
| JP | 11008068 | 1/1999 |
| JP | 11111458 | 4/1999 |
| JP | 2002060742 | 2/2002 |
| JP | 2002167578 | 6/2002 |
| JP | 2003138251 | 5/2003 |
| JP | 2004091444 | 3/2004 |
| JP | 2005281210 | 10/2005 |
| JP | 2006028055 | 2/2006 |
| JP | 2006114844 | 4/2006 |
| WO | WO-0003565 | 1/2000 |

OTHER PUBLICATIONS

Roth et al. Mater. Res. Soc. Symp. Proc. vol. 871E, 2005.* MRS Website, Symposium I: Organic Thin-Film Electronics (Spring 2005 Program) (http://www.mrs.org/s_mrs/doc.asp?CID=2091 &DID=95086), 2005.*
Federal Register Notice, vol. 77, No. 91, Thursday, May 10, 2012, pp. 27443-27444.*

* cited by examiner

*Primary Examiner* — Joseph Kosack
*Assistant Examiner* — Matthew Coughlin
(74) *Attorney, Agent, or Firm* — Jonathan Myers; Andrew Wilford

(57) ABSTRACT

Described are oligotetracenes of formula I which may either be unsubstituted or carry one or more substituents R and

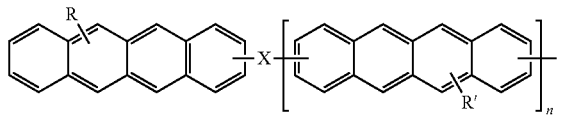

Figure 1A:
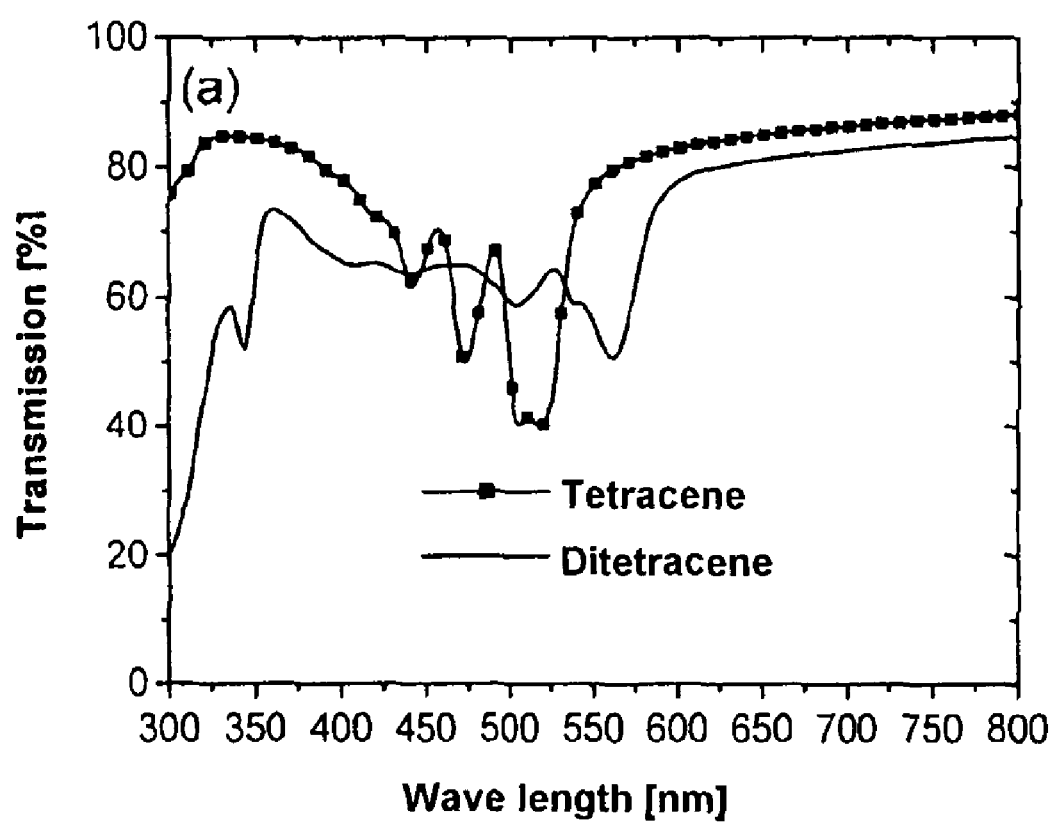

R' which are selected from the group comprising
- halogen,
- CN,
- alkyl or alkoxy radicals containing 1 to 18 carbon atoms,
- aryl radicals containing up to 10 carbon atoms which may also contain one or more heteroatoms, and/or
- fluorinated or perfluorinated alkyl or alkoxy radicals containing 1 to 18 carbon atoms, where n is an integer from 1 to 20, preferably 1 to 6, very particularly preferably 1 or 2, and X stands for a single bond, an alklyene group containing 1 to 6 carbon atoms, a hydrocarbon chain having one or more conjugated double bonds, an aryl group, or a system composed of one or more condensed aromatic rings. In the oligotetracenes according to the invention, one or more of the condensed aromatic six-atom rings may be substituted by a five-atom ring which may also contain a heteroatom.

Also described is a method for preparing the referenced oligotetracenes, and use thereof as semiconductors in organic field-effect transistors (OFET's), organic light-emitting diodes (OLED's), sensors, and organic solar cells.

5 Claims, 5 Drawing Sheets

OLIGO-TETRACENES, PRODUCTION AND USE THEREOF

CROSS REFERENCE TO RELATED APPLICATIONS

This application is the US national phase of PCT application PCT/EP2006005926, filed 21 Jun. 2006, published 4 Jan. 2007 as WO 2007/000268, and claiming the priority of German patent application 102005029574.6 itself filed 25 Jun. 2005, whose entire disclosures are herewith incorporated by reference.

The invention relates to substituted and unsubstituted oligotetracenes, preparation of same, and use thereof as semiconductors in organic field-effect transistors (OFET's), organic light-emitting diodes (OLED's), sensors, organic solar cells, and in other areas of optics and electronics.

It is known that the display, processing, and storage of information is a fundamental basis of a society dominated by technical information. All means necessary for assisting such processes must be made continually smaller, better, and more economical. This constant development of information technology is associated with increased use of organic instead of inorganic materials. Organic materials are generally less costly and easier to process. In addition, the ever-increasing number of publications and patents in the field of information technology demonstrates that, contrary to the view largely held heretofore, organic materials may perform the same functions as inorganic materials, or even additional functions, for the transport and conversion of electrical charge or electromagnetic radiation. Furthermore, the problems associated with the lower stability of organic materials under the severe conditions of manufacturing and use have been increasingly reduced in the meantime. Thus, many organic materials may currently be used as components in light-emitting diodes, solar cells, and in optical switches and thin-layer transistors. Organic field-effect transistor (OFET's) allow the use of economical, light, and flexible plastic materials as an alternative to glass in liquid-crystal screens and in displays equipped with light-emitting diodes.

The organic material most thoroughly investigated and usable for semiconductors in organic field-effect transistors to date is α-sexithienyl. Unfortunately, the field-effect mobility and the on-off ratio for most practical applications of this material are not adequate: The typical field-effect mobility of α-sexithienyl-based OFET's is 0.03 $cm^2/V\times s$, and the on-off ratio is approximately $10^6$, whereas in amorphous hydrogenated silicone the 0.10 field-effect mobility is greater than 0.5 $cm^2/V\times s$ and the on-off ratio is greater than $10^8$. Significant improvements have nevertheless been made using organic semiconductors: a very promising substance is pentacene. It has recently been reported that organic field-effect transistors (OFET's) made using pentacene achieve a field-effect mobility greater than 0.5 $cm^2/V\times s$ and an on-off ratio greater than $10^8$ (1). Both results are comparable to those for hydrogenated amorphous silicones, and are the best currently available for organic field-effect transistors. However, pentacenes have the significant disadvantage that they are chemically unstable, oxidize easily, and disproportionate, thus undergoing cycloaddition reactions (2-4). Pentacene must therefore be purified and handled with great care under inert conditions. Furthermore, the chemical derivatization of pentacene is very difficult due to its sensitivity, which does not permit the use of common aromatic substitution reactions. Each derivative, if it is available at all, therefore requires individual synthesis. Systematic tests and optimizations of pentacene derivatives for organic field-effect transistors (OFET's) are therefore very difficult.

The object, therefore, is to develop substances that have the good electrical properties of pentacene but that are more easily obtainable and easier to purify, and that may also be used in conventional manufacturing processes for organic semiconductors. In order to maximize efficiency in achieving this object, it has been necessary to identify crucial parameters responsible for the superior properties of pentacene-based OFET's. A relationship between the high mobility of the charge carriers and the high molecular ordering in pentacene films has also been recently reported. Furthermore, pentacene appears to crystallize in molecular configurations in which the individual condensed aromatic ring systems occupy alternating positions and orientations, which is virtually ideal for the movement of charge carriers over long distances. Lastly, the level of the highest occupied molecular orbital (HOMO) (5.07 eV) is well-adapted to gold, which is usually used as the material for anodes and cathodes. On the other hand, tetracene, which is composed of four instead of five condensed benzene rings, is much more stable chemically but has much less satisfactory semiconductor properties. OFET's based on polycrystalline tetracenes generally have field-effect mobilities of 0.05 $cm^2/V\times s$ and an on-off ratio of approximately $10^6$. However, tetracene has an equally satisfactory delocalized n-electron system which is very similar to that of pentacene. Therefore, the enormous differences between the semiconducting properties of the two substances are not easy to understand. One explanation could lie in the less advantageous or less complete molecular orientation in tetracene thin layers and deeper HOMO layers, which makes it difficult to introduce holes with a metal electrode. The HOMO level of polycrystalline tetracene is approximately 5.4 eV (5), which means that it is not possible to make an effective barrier to the injection of holes with metal electrodes. To test this working hypothesis, several strategies have been developed which allow the molecular configurations in thin tetracene layers to be increased or possibly modified without losing their chemical stability. A higher molecular ordering could also increase the number of exchange reactions between the molecules the HOMO.

One way to achieve this objective could involve lengthening the tetracene since an important distinction between tetracene and pentacene is that tetracene is shorter. This could be the reason for lower ordering and less advantageous transistor properties. If this assumption is valid, the present problem could possibly be solved by increasing the length of the tetracene molecule without impairing its chemical and semiconductive properties. The addition of hydrocarbons or simple aromatic groups to the longitudinal axis of the tetracenes is therefore probably not the best approach, since this could result in a decrease in the conductive properties and disturbances of the advantageous orientation of the tetracene molecules combined with increased sensitivity of the molecules to oxidation. One promising alternative which is conceptually simpler but nevertheless successful could be to join two tetracene molecules, thereby producing a significantly longer molecule. This strategy would also prevent introduction of any differing chemical substances into the system and, due to the angle between the two joined tetracene molecules, at least in the dissolved state, there would also possibly be no significant changes in stability during manufacture or purification. On the other hand, after deposition onto a thin layer a certain planarization is expected in the solid state which could result in improved mobility and lower ionization energy compared to the original tetracene.

Of course, these considerations appear to be fairly simple because such an extensive change in the shape of the tetracene may have important, unexpected consequences for the orientation of the molecules which also influence the mobility of the charges. On the other hand, there would be some possibility of greatly improving the transistor properties. For this reason the concept of developing test devices from ditetracene has been developed. The manner in which these novel organic molecules may be prepared and the properties thereof in organic field-effect transistors has also been demonstrated. The invention therefore relates to the tetracenes of formula I

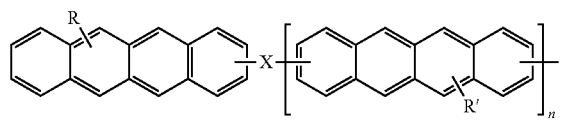

that may either be unsubstituted or carry one or more substituents R and R' which are selected from the group comprising
  halogen,
  CN,
  alkyl or alkoxy radicals containing 1 to 18 carbon atoms,
    aryl radicals containing up to 10 carbon atoms which may also contain one or more
  heteroatoms, and/or
  fluorinated or perfluorinated alkyl or alkoxy radicals containing 1 to 18 carbon atoms,
where n is an whole number from 1 to 20, preferably 1 to 6, very particularly preferably 1 or 2, and X stands for a single bond, an alkylene group containing 1 to 6 carbon atoms, a hydrocarbon chain having one or more conjugated double bonds, an aryl group, or a system composed of one or more condensed aromatic rings. In the oligotetracenes according to the invention, one or more of the condensed aromatic six-atom rings may be replaced by a five-atom ring which may also contain a heteroatom.

In the oligotetracene according to the invention the bridging aryl group may be one or more phenyl rings which are unsubstituted or substituted with alkyl groups containing 1 to 18 carbon atoms, a five-member ring containing a heteroatom, or a ferrocenylene unit.

One particularly preferred oligotetracene is 2-(tetracene-2-yl)tetracene of formula II

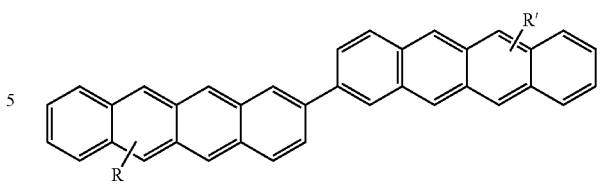

here R and R' may be hydrogen or have the meanings given for formula I.

A further preferred ditetracene corresponds to formula III

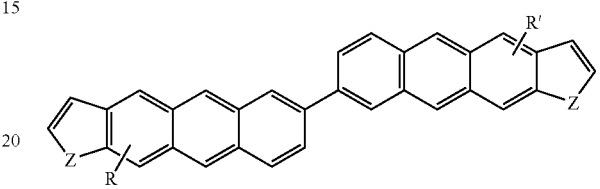

A further preferred ditetracene corresponds to formula III where R and R' may be hydrogen or have the meanings given for formula I.

The above-referenced oligotetracenes and ditetracenes are prepared by oligomerization or dimerization of the corresponding tetracenes, for example by means of a coupling reaction controlled by transition metals. These methods typically require halogenated starting materials. A tetracene derivative is therefore required which contains a chlorine or bromine atom in the 2-position. Direct selective bromination of the tetracene resulting in such a derivative is not possible. A new method for preparing 2-bromotetracene has therefore been developed. A preferably halogenated, in particular brominated, tetracene which is singly or multiply substituted in any given position, in particular in the 1-, 2-, or 4-position, is oligomerized. Particularly preferred is the oligomerization of a tetracene substituted in the 2-position by use of an organometallic compound in a cross-coupling reaction (Suzuki or Stille reaction, for example). The resulting product is then purified by vacuum sublimation.

The synthesis of a tetracene brominated in the 2-position is shown by way of example in the following illustration:

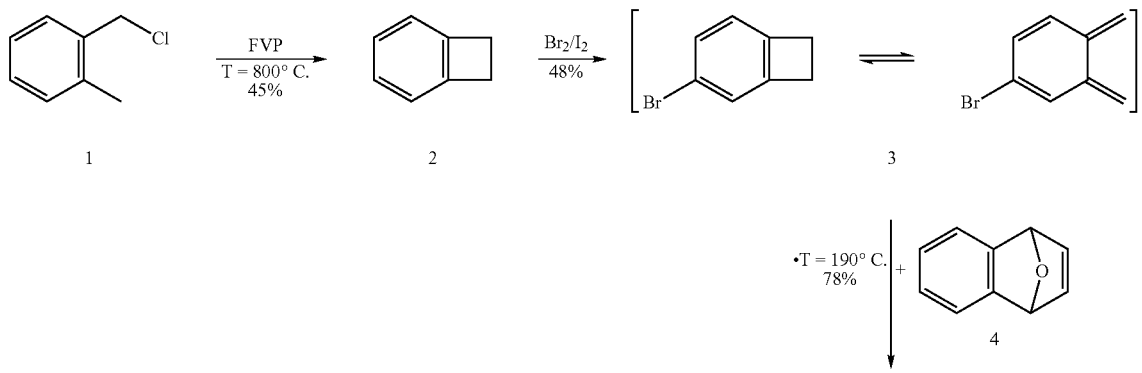

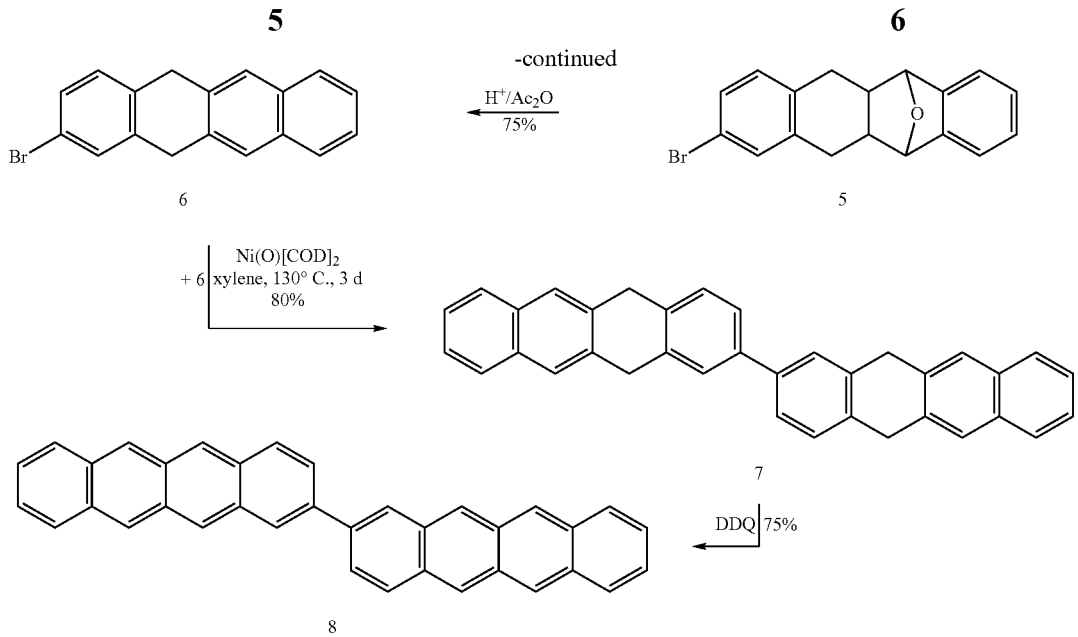

In a first step, α-chloro-o-xylene 1 was subjected to pyrolysis at approximately 800° C. and 0.5 mbar. Benzocyclobutene 2 was obtained in a 45% yield. The selective bromination thereof was carried out by treating benzocyclobutene, dissolved in acetic acid, with a mixture of bromine and iodine at room temperature, resulting in 4-bromobenzocyclobutene 3. Dissolving in toluene and heating with a slight molar excess of 1,4-dihydro-1,4-epoxynaphthalene 4 at 220° C. for 20 hours resulted in an 80% yield of a pure endo/exo mixture of the Diels-Alder addition product 5, a colorless crystalline material. This material was heated at reflux in acetic anhydride in the presence of concentrated hydrochloric acid, thus forming 9-bromo-6,11-dihydrotetracene 6. The Yamamoto coupling then resulted in 2-(5,12-dihydrotetracene-2-yl)-5,12-dihydrotetracene 7. The coupling reaction was carried out in an approximately 80% yield in a mixture of dimethylformamide and toluene at 80° C., using bis(cyclooctadienyl)nickel(0) in stoichiometric quantities. After recrystallization from o-dichlorobenzene, compound 7 was dehydrogenated by treatment with 2,3-dichloro-5,6-dicyano-p-benzoquinone (DDQ) in boiling o-xylene. After purification by repeated vacuum sublimation, orange-red crystals of 2-(tetracene-2-yl) tetracene 8 were obtained in a yield of 75%. All intermediate products were characterized by $^1H$ and $^{13}C$ NMR spectroscopy and mass spectroscopy. Compound 8 was characterized by UV-visible spectroscopy.

Figure 1B:
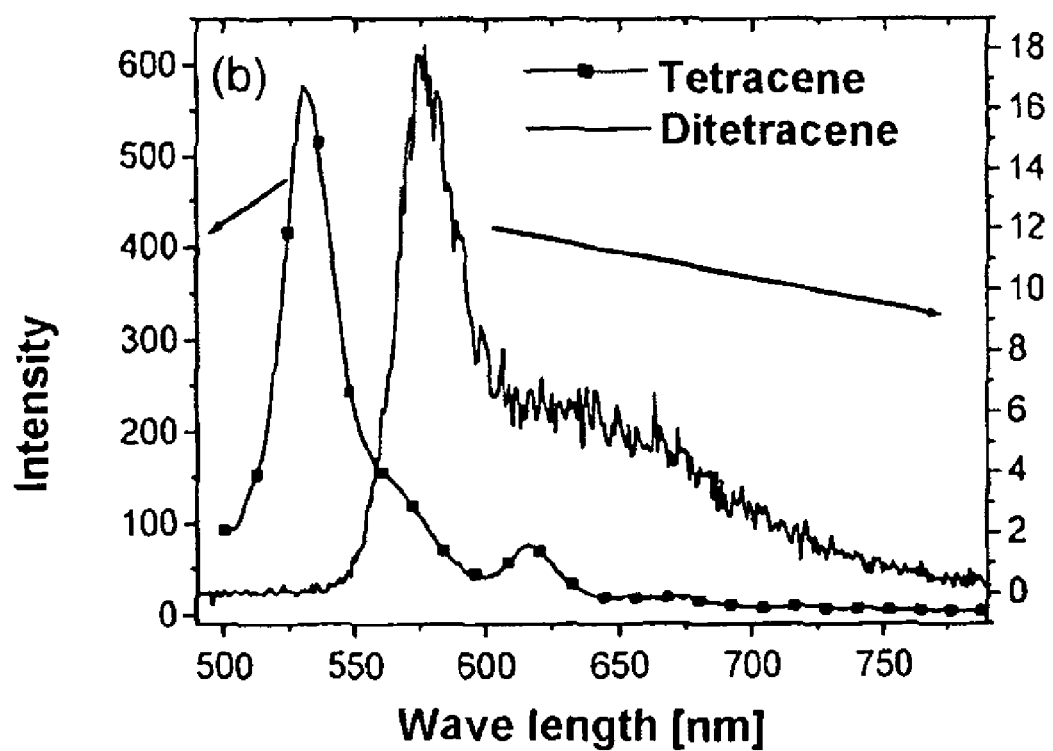

FIG. 1A shows a representative spectrum recorded in a thin layer of 8 on a quartz semiconductor wafer. FIG. 1B additionally shows the photoluminescence spectrum of 8 upon excitation with light having a wavelength of λ=345 nm.

In general it may be stated that the synthesis of the oligo- and ditetracenes according to the invention may be carried out in a particularly successful manner when a tetracene that is halogenated, preferably brominated, in the 2-position is oligomerized or dimerized. Particularly suited for this purpose is the dimerization using, for example, organoboron compounds in a cross-coupling reaction, which is well known in the field of chemistry as the Suzuki or Stille reaction.

The above-described ditetracenes may advantageously be used as semiconductors in organic field-effect transistors (OFET's). The following procedure, for example, is practical:

To use the ditetracenes according to the invention that have been purified by repeated vacuum sublimation, devices were manufactured in which these materials were used as semiconductors in OFET's. The device described in FIG. 2 was used.

Figure 2:
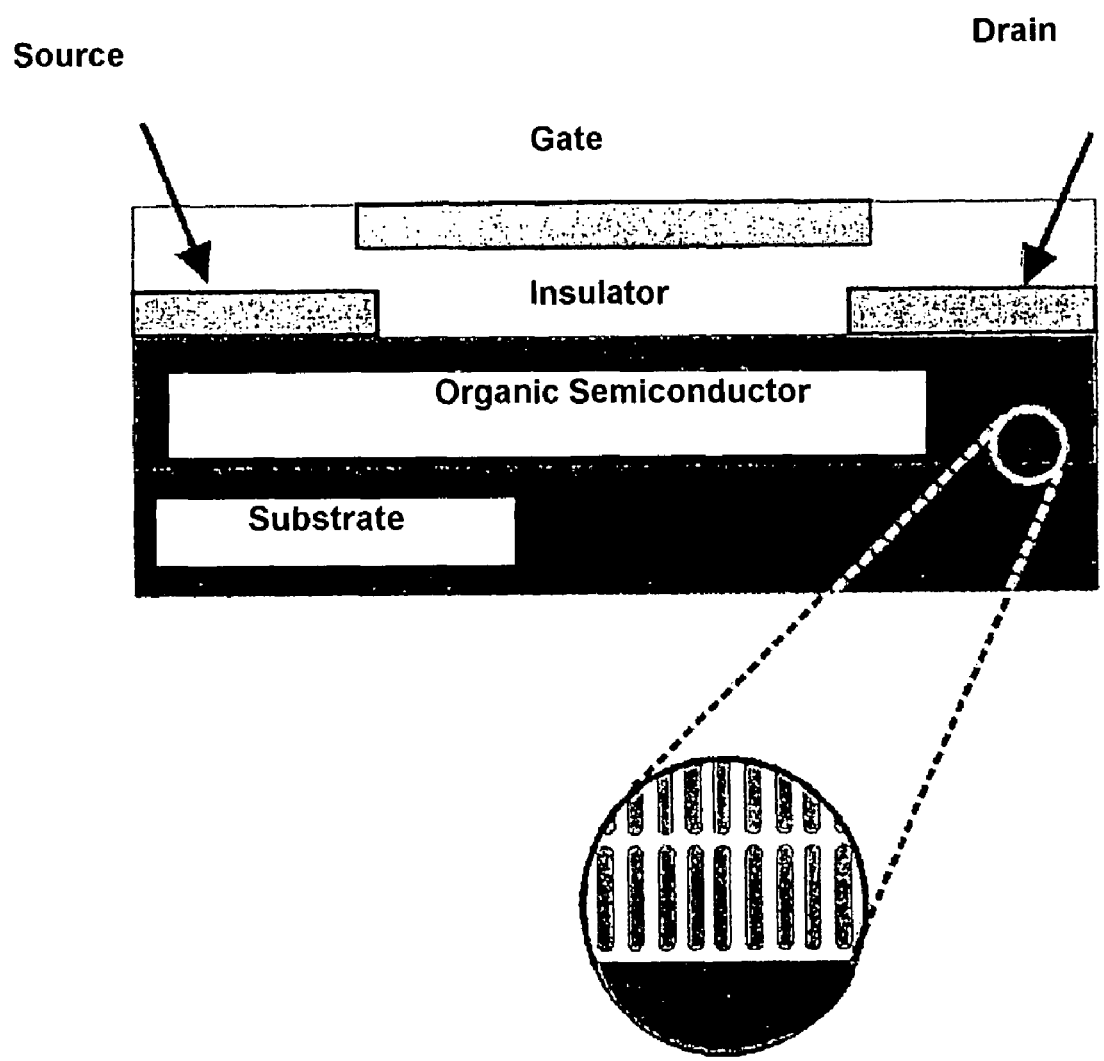

The OFET's according to the invention were covered with strongly doped n-type silicone materials (3-5 ohm×cm resistance), using thermally produced $SiO_2$ having a layer thickness of approximately 230 nm. A thin chromium layer was precipitated onto the entire surface, and a gold layer 50 nm thick was applied thereto. The gold electrodes were photolithographically textured. The gold electrodes were interdigitally configured with channel lengths of L=7 μm and a channel width of W=20 cm. The design of the transistor electrodes is also shown in FIG. 2.

Figure 3:
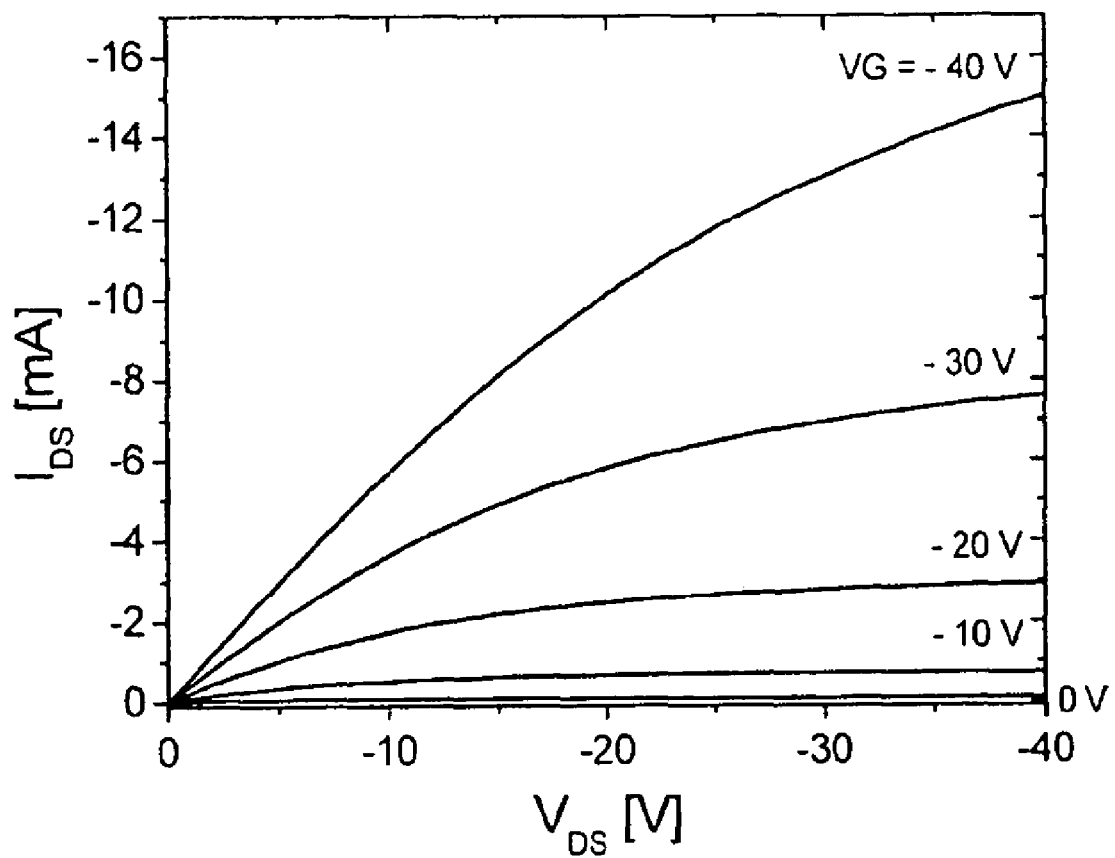

In some cases the $SiO_2$ surface was treated with a silane coupling reagent to improve the homogeneity of the organic film and the substrate cover. The substrates thus produced were directly inserted into a vacuum chamber while avoiding the effect of ambient air. The ditetracene 8 was thermally precipitated onto the prepared structures at room temperature or at 140° C. and a pressure of $1×10^{-6}$ mbar. The electrical characterization was carried out using an HP 4155A analyzer for semiconductor properties in an inert atmosphere. The organic field-effect transistors produced in the form of semiconductors using ditetracene were tested for their characteristic properties on standard devices having an untreated $SiO_2$ surface. The representative properties are shown in FIG. 3.

The curves show the characteristic properties of unipolar field-effect transistors having good saturation properties.

Figure 4:
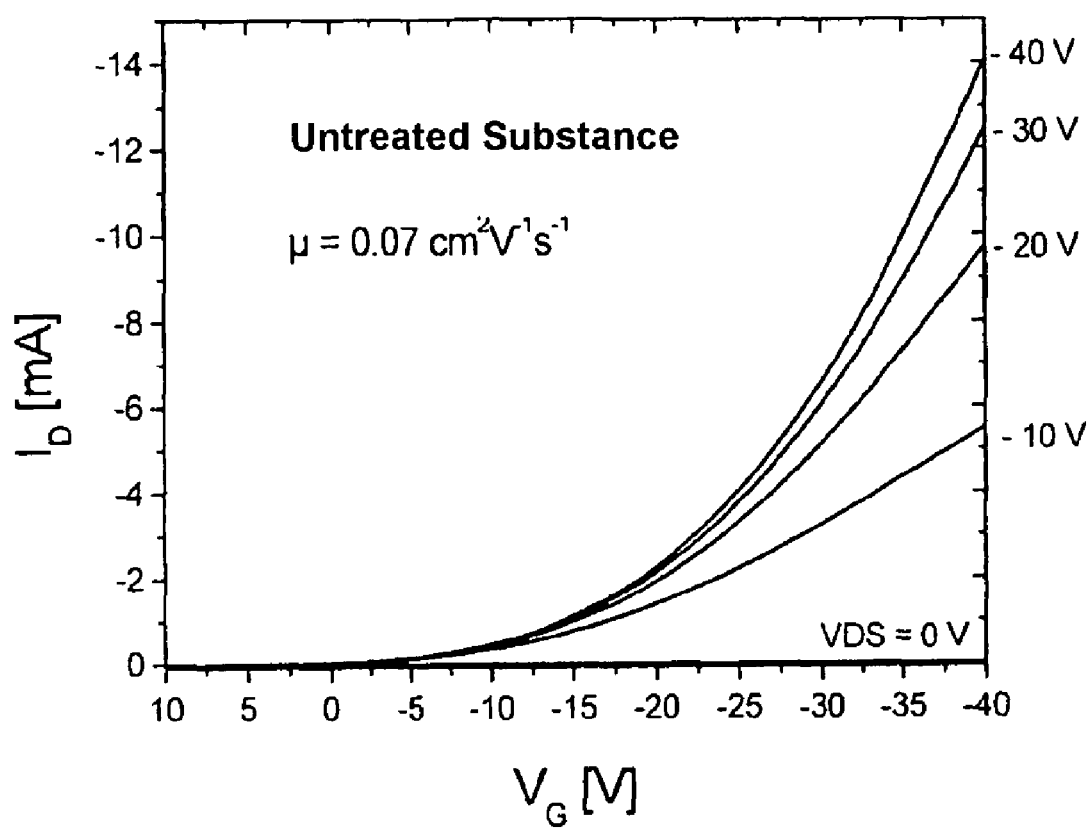

The electrical transfer properties shown in FIG. 4 were used for further evaluation.

In a saturated state the current may be described by the Shockley equation:

$$|I_D| = \frac{WC^*}{2L}\mu_h(V_G - V_{th})^2$$

in which
C'=capacitance of the insulator
L=channel length $\mu_h$=charge carrier mobility (holes)
$V_G$=gate voltage
$V_{TH}$=threshold voltage
W=channel width The method according to the invention thus provides an efficient and very generally applicable synthesis option by which bis(tetracenyl) aromatics may be prepared. These compounds are suited for high-efficiency field-effect transistors having increased charge mobility. In some derivatives the charge mobility reaches values of up to $\mu_h$=0.5 cm²/V×s. These derivatives may also be used for organic light-emitting diodes (OLED's), sensors, and organic solar cells.

LITERATURE REFERENCES (1) C. D. Dimitrakopoulos and Patrick R. L. Malenfant, Adv. Mater. 2002, 14, No. 2, January 2001.
(2-4) J. E. Northrup and M. L. Chabinyc, Phys. Rev. 68, 041202 (2003), D. V. Lange, X. Chi, T. Siegrist, A. M. Sergent, A. R. Ramirez, Phys. Rev. Lett. 93 (7), Art. No. 077601, Aug. 15, 2004
Ch. Pannemann, T. Diekmann, and U. Hillerungmann, J. Mater. Res., Vol. 19, No. 7, July 2004.
(5) Electrical Processes in Organic Crystals and Polymers, by Martin Pope; Charles E. Swenberg, Oxford Univ. Pr., Jun. 1, 1982.

The invention claimed is:

1. A compound of the Formula (Ia)

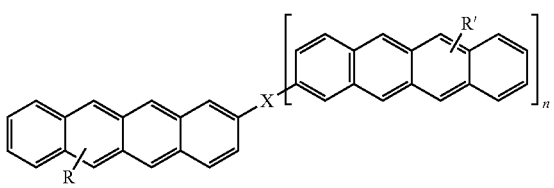

wherein
R and R' are each at least one substituent selected from the group consisting of hydrogen, halogen, CN, $C_1$ to $C_{18}$ alkyl, $C_1$ to $C_{18}$ alkoxy, aryl radicals containing up to 12 carbon atoms which optionally contains one or more heteroatoms, fluorinated $C_1$ to $C_{18}$ alkyl, fluorinated $C_1$ to $C_{18}$ alkoxy, perfluorinated $C_1$ to $C_{18}$ alkyl, and perfluorinated $C_1$ to $C_{18}$ alkoxy;

n is an integer from 1 to 20, and
X is a single bond, a hydrocarbon chain having multiple conjugated double bonds, or a ferrocenylene unit.

2. A compound of the Formula (II)

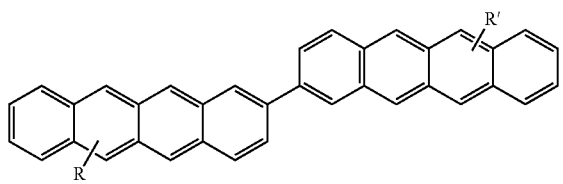

wherein R and R' are each at least one substituent selected from the group consisting of hydrogen, halogen, CN, $C_1$ to $C_{18}$ alkyl, $C_1$ to $C_{18}$ alkoxy, aryl radicals containing up to 12 carbon atoms which optionally contains one or more heteroatoms, fluorinated $C_1$ to $C_{18}$ alkyl, fluorinated $C_1$ to $C_{18}$ alkoxy, perfluorinated $C_1$ to $C_{18}$ alkyl, and perfluorinated $C_1$ to $C_{18}$ alkoxy.

3. The compound of the Formula (II) defined in claim 2 wherein R and R' are each hydrogen.

4. A compound of the Formula (III)

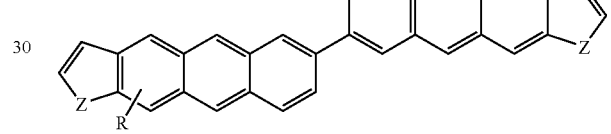

wherein Z is O, S or NH, and
R and R' are each at least one substituent selected from the group consisting of hydrogen, halogen, CN, $C_1$ to $C_{18}$ alkyl, $C_1$ to $C_{18}$ alkoxy, aryl radicals containing up to 12 carbon atoms which optionally contains one or more heteroatoms, fluorinated $C_1$ to $C_{18}$ alkyl, fluorinated $C_1$ to $C_{18}$ alkoxy, perfluorinated $C_1$ to $C_{18}$ alkyl, and perfluorinated $C_1$ to $C_{18}$ alkoxy.

5. The compound of the Formula (III) defined in claim 4 wherein R and R' are each hydrogen.

* * * * *